United States Patent [19]

Adams et al.

[11] Patent Number: 5,648,337
[45] Date of Patent: *Jul. 15, 1997

[54] ANTIHERPES PENTAPEPTIDES

[75] Inventors: Julian Adams, Ridgefield, Conn.; Pierre Louis Beaulieu, Montreal, Canada; Pierre Lavallée, Rosemere, Canada; Raymond Plante, Laval, Canada; Sumanas Rakhit, Dollard des Ormeaux, Canada

[73] Assignee: Bio-Mega/Boehringer Ingelheim Research Inc., Laval, Canada

[*] Notice: The term of this patent shall not extend beyond the expiration date of Pat. No. 5,502,036.

[21] Appl. No.: 90,681

[22] Filed: Jul. 13, 1993

Related U.S. Application Data

[63] Continuation of Ser. No. 915,968, Jul. 16, 1992, abandoned, which is a continuation of Ser. No. 864,736, Apr. 7, 1992, abandoned, which is a continuation of Ser. No. 547,271, Jul. 3, 1990, abandoned.

[51] Int. Cl.$^6$ ............................ A61K 38/00; C07K 5/00; C07K 7/00
[52] U.S. Cl. ........................... 514/17; 514/12; 530/300; 530/330
[58] Field of Search .................. 514/12, 17; 530/300, 530/330

[56] References Cited

U.S. PATENT DOCUMENTS 4,795,740  1/1989  Cohen et al. .

*Primary Examiner*—Avis M. Davenport
*Attorney, Agent, or Firm*—R. P. Raymond; M-E. M. Devlin; A. R. Stempel

[57] ABSTRACT

Disclosed herein are pentapeptide derivatives of the formula (SEQ ID NO: 24) $XNR^1—CH(R^2)—C(O)—NH—CH(R^3—C(O)—NR^4—CH(CH_2Y)—CO—NH—CH[CR^5(R^6)—COOH]—C(W)—NH—CH(R^7)—Z$ wherein X is a terminal group, for example, alkanoyl or phenylalkanoyl radicals, $R^1$ is alkyl or phenylalkyl, $R^2$, $R^3$ and $R^7$ are selected from the side chains of amino acid or derived amino acid residues, $R^4$, $R^5$, and $R^6$ are hydrogen or lower alkyl, W is oxo or thioxo, Y is carboxy, carbamyl or 5-1H-tetrazolyl and Z is carboxy or 5-1H-tetrazolyl. The derivatives are useful for treating herpes infections.

6 Claims, No Drawings

ANTIHERPES PENTAPEPTIDES

This is a continuation of application Ser. No. 07/915,968 (abandoned) filed Jul. 16, 1992 which is a continuation application of Ser. No. 07/864,736 (abandoned) filed Apr. 7, 1992, which is a continuation application of Ser. No. 07/547,271 (abandoned) filed Jul. 3, 1990.

FIELD OF THE INVENTION

This invention relates to peptide derivatives having antiviral properties and to means for using the derivatives to treat viral infections. More specifically, the invention relates to peptide derivatives (hereinafter called "peptides") exhibiting activity against herpes viruses, to pharmaceutical compositions comprising the peptides, and to a method of using the peptides to treat herpes infections.

BACKGROUND OF THE INVENTION

The family of herpes viruses is responsible for a wide range of infections that afflict humans and many important domestic animals. The diseases caused by these viruses range from bothersome cold sores to highly destructive infections of the central nervous system (encephalitis). The more common members of this family include herpes simplex virus (types 1 and 2) responsible for (SEQ ID NO:1) cold sores and genital lesions; varicella zoster virus which causes chicken pox and shingles; and Epstein-Barr virus which causes infectious mononucleosis. Although some significant advances have been made in the last decade in antiviral therapy, the need for effective, safe therapeutic agents for treating herpes viral infections continues to exist For a recent review of current therapeutic agents in this area, see M. C. Nahata, "Antiviral Drugs: Pharmacokinetics, Adverse Effects and Therapeutic Use", J. Pharm. Technol., 3, 100 (1987).

The present application discloses a group of peptide derivatives having activity against herpes viruses. The relatively selective action of these peptides against herpes viruses, combined with a wide margin of safety, renders the peptides as desirable agents for combating herpes infections.

The association of peptides with anti-herpes activity is uncommon. Instances of reports of such an association include B. M. Dutia et at., Nature, 321, 439 (1986), E. A. Cohen et at., Nature, 321, 441 (1986), J. H. Subak-Sharpe et al., UK patent application 2185024, published Jul. 8, 1987, E. A. Cohen et al., European patent application 246630, published Nov. 25, 1987, R. Freidinger et at., European patent application 292255, published Nov. 23, 1988, and R. Freidinger et al., U.S. Pat. No. 4,814,432, issued Mar. 21, 1989. The subject peptides of the previous reports can be distinguished from the peptides of the present application by characteristic structural and biological differences.

SUMMARY OF THE INVENTION

The peptides of this invention are represented by formula 1

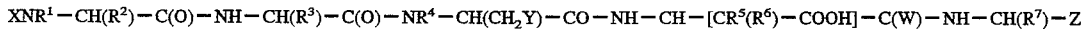

wherein X is (1-10C)alkanoyl, (1-10C)alkoxycarbonyl, benzoyl, benzoyl monosubstituted or disubstituted with a substituent selected from halo, hydroxy, lower alkyl, lower alkoxy, phenyl, 2-carboxyphenyl or benzyl, 2,2-diphenylacetyl, phenyl(2-10C)alkanoyl or phenyl(2-10C) alkanoyl monosubstituted or disubstituted on the aromatic portion thereof with a substituent selected from halo, hydroxy, lower alkyl, lower alkoxy or phenyl;

$R^1$ is lower alkyl or phenyl(lower)alkyl;
$R^2$ is lower alkyl or hydroxy(lower)alkyl;
$R^3$ is hydrogen, lower alkyl, hydroxy(lower)alkyl, mercapto(lower)alkyl, methoxy(lower)alkyl, methylthio(lower)alkyl, lower cycloalkyl or (lower cycloalkyl)methyl;
$R^4$, $R^5$ and $R^6$ each independently is hydrogen or lower alkyl;
$R^7$ is lower alkyl;
W is oxo or thioxo;
Y is carboxy, carbamyl or 5-1H-tetrazolyl; and
Z is carboxy or 5-1H-tetrazolyl; or a therapeutically acceptable salt thereof.

A preferred group of the peptides of this invention is represented by formula 1 wherein X is (1-10C)alkanoyl, (1-10C)alkoxycarbonyl, benzoyl, benzoyl monosubstituted with halo, hydroxy, lower alkyl, lower alkoxy, phenyl, 2-carboxyphenyl or benzyl, 2,2-diphenylacetyl, phenyl(2-10C)alkanoyl or phenyl(2-10C)alkanoyl monosubstituted or disubstituted on the aromatic portion thereof with a substituent selected form halo, hydroxy, lower alkyl or lower alkoxy; and $R^1$, $R^2$, $R^3$, $R^4$, $R^5$, $R^6$, $R^7$, W, Y and Z are as defined hereinabove; or a therapeutically acceptable salts thereof.

A more preferred group of peptides is represented by formula 1 wherein X, $R^1$, $R^2$ and $R^7$ are as defined in the last instance; $R^3$ is hydrogen, lower alkyl, hydroxy(lower)alkyl, methoxy(lower)alkyl, lower cycloalkyl or (lower cycloalkyl)methyl; $R^4$, $R^5$ and $R^6$ each independently is hydrogen or methyl; Y is carbamyl or 5-1H-tetrazolyl; and Z is carboxy or 5-1H-tetrazolyl; or a therapeutically acceptable salt thereof.

A most preferred group of the peptides is represented by formula 1 wherein X is acetyl, 4-methylpentanoyl, benzoyl, 2-biphenylylcarbonyl, 2-(phenylmethyl)benzoyl, 2,2-diphenylacetyl, phenylacetyl, phenylpropionyl or (4-hydroxyphenyl)propionyl; $R^1$ is methyl, ethyl, 2-methylpropyl or 2-phenylethyl; $R^2$ is 1-methylethyl, 1-methylpropyl or 1-hydroxyethyl; $R^3$ is lower alkyl, hydroxymethyl, 1-hydroxyethyl, 1-methoxyethyl, cyclopentyl or cyclohexylmethyl; $R^4$ is hydrogen or methyl, $R^5$ and $R^6$ are hydrogen; $R^7$ is 2-methylpropyl; and Y and Z are as defined in the last instance; or a therapeutically acceptable salt thereof.

Included within the scope of this invention is a pharmaceutical composition comprising an anti-herpes vitally effective amount of a peptide of formula 1, or a therapeutically acceptable salt thereof, and a pharmaceutically or veterinarily acceptable carrier.

Also included within the scope of this invention is a cosmetic composition comprising a peptide of formula 1, or a therapeutically acceptable salt thereof, and a physiologically acceptable carrier suitable for topical application.

An important aspect of the invention involves a method of treating herpes viral infections in a mammal by administering to the mammal an anti-herpes virally effective amount of the peptide of formula 1, of a therapeutically acceptable salt thereof.

Another important aspect involves a method of inhibiting the replication of herpes virus by contacting the virus with a herpes vital ribonucleotide reductase inhibiting amount of the peptide of formula 1, or a therapeutically acceptable salt thereof.

Processes for preparing the peptides of formula 1 are described hereinafter.

DETAILS OF THE INVENTION

GENERAL

Alternatively, formula 1 can be illustrated as:

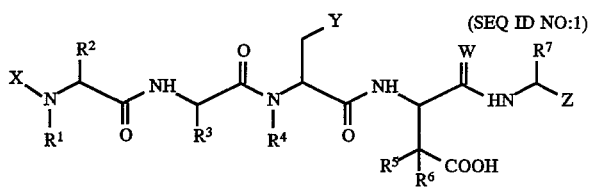

(SEQ ID NO:1)

The term 'residue' with reference to an amino acid or amino acid derivative means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commision of Biochemical Nomenclature, see European Journal of Biochemistry 138, 9 (1984). For instance, Gly, Vat, Thr, Ala, Ile, Asp, Ser and Leu represent the residues of glycine, L-valine, L-threonine, L-alanine, L-isoleucine, L-aspartic acid, L-serine and L-leucine, respectively.

The asymmetric carbon atoms residing in the principal linear axis (i.e. the backbone) of the peptides of formula 1, exclusive of the terminal groups, have an S configuration. Asymmetric carbon atoms residing in the side chain of an amino acid or derived amino acid residue, including those in terminal groups, may also have the R configuration. Furthermore, with respect to disubstituted benzoyl and disubstitued phenyl(1-10C)alkanoyl as defined for X of peptides of formula 1, the substituents are selected on the basis that they do not interfere with each others presence.

The term 'halo' as used herein means a halo radical selected from bromo, chloro, fluoro or iodo.

The term "lower alkyl" as used herein, either alone or in combination with a radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1, 1-dimethylethyl.

The term "lower cycloalkyl" as used herein, either alone or in combination with a radical, means saturated cyclic hydrocarbon radicals containing from three to six carbon atoms and includes cyclopropyl, cyclobutyl, cyclopentyl and cyclohexyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tertiary-butyloxy.

The term "(1-10C)alkoxy" as used herein, either alone or in combination with a radical, means straight and branched chain alkoxy radicals containing from one to ten carbon atoms. The term "(1-10C)alkanoyl" as used herein means straight or branched chain 1-oxoalkyl radicals containing for one to ten carbon atoms; for example, acetyl, 4-methyl-1-oxopentyl (or 4-methylpentanoyl) or 1-oxooctyl (or octanoyl). The term "phenyl(2-10)alkanoyl" as used herein means phenyl substituted 1-oxoalkyl radicals wherein the 1-oxoalkyl portion thereof is a straight or branched chain 1-oxoalkyl containing from two to ten carbon atoms; for example, 1-oxo-3-phenylpropyl and 1-oxo-5-methyl-6-phenylhexyl.

The symbol "ψ[CSNH]" used between the three-letter representations of two amino acid residues means that the normal amide bond between those residues in the peptide, being represented, has been replaced with a thioamide bond.

The term "pharmaceutically acceptable carrier" or "veterinarily acceptable carrier" as use herein means a non-toxic, generally inert vehicle for the active ingredient which does not adversely affect the ingredient.

The term "physiologically acceptable carrier" as used herein means an acceptable cosmetic vehicle of one or more non-toxic excipients which do not react with or reduce the effectiveness of the active ingredient contained therein.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "effective amount" means a predetermined antiviral amount of the antiviral agent, i.e. an amount of the agent sufficient to be effective against the viral organisms in vivo.

The term "coupling agent" as used herein means an agent capable of effecting the dehydrative coupling of an amino acid or peptide free carboxy group with a free amino group of another amino acid or peptide to form an amide bond between the reactants. The agents promote or facilitate the dehydrative coupling by activating the carboxy group. Descriptions of such coupling agents and activated groups are included in general text books of peptide chemistry; for instance, E. Schroder and K. L. Lubke, "The Peptides", Vol. 1, Academic Press, New York, N.Y., 1965, pp 2-128, and K. D. Kopple, "Peptides and Amino acids", W. A. Benjamin, Inc., New York, N.Y., 1966, pp 33–51. Examples of coupling agents are thionyl chloride, diphenylphosphoryl azide, 1,1'-caxbonyldiimidazole, dicyclohexylcarbodiimide, N-hydroxysuccinimide, or 1-hydroxybenzotriazole in the presence of dicyclohexylcarbodiimide. A very practical and useful coupling agent is (benzotriazol-1-yloxy)tris (dimethylamino)-phosphonium hexafluorophosphate, described by B. Castro et al., Tetrahedron Letters, 1219 (1975), see also D. Hudson, J. Org. Chem., 53, 617 (1988), either by itself or in the presence of 1-hydroxybenzotriazole.

Process

The peptides of formula 1 can be prepared by processes which incorporate therein methods commonly used in peptide synthesis such as classical solution coupling of amino acid residues and/or peptide fragments, and if desired solid phase techniques. Such methods are described, for example, by E. Schroder and K. Lubke, cited above, in the textbook series, "The Peptides: Analysis, Synthesis, Biology", E. Gross et at., Eds., Academic Press, New York, N.Y., 1979–1987, Volumes 1 to 8, and by J. M. Stewart and J. D. Young in "Solid Phase Peptide Synthesis", 2nd ed., Pierce Chem. Co., Rockford, IL, USA, 1984.

A common feature of the aforementioned processes for the peptides is the protection of the reactive side chain groups of the various amino acid residues or derived amino acid residues with suitable protective groups which will prevent a chemical reaction from occurring at that site until the protective group is ultimately removed. Usually also common is the protection of an α-amino group on an amino acid or a fragment while that entity reacts at the carboxy group, followed by the selective removal of the α-amino protective group to allow subsequent reaction to take place at that location. Usually another common feature is the initial protection of the C-terminal carboxyl of the amino acid residue or peptide fragment, if present, which is to become the C-terminal function of the peptide, with a suitable protective group which will prevent a chemical reaction from occurring at that site until the protective group is removed after the desired sequence of the peptide has been assembled.

In general, therefore, a peptide of formula 1 can be prepared by the stepwise coupling in the order of the sequence of the peptide of the amino acid or derived amino acid residues, or fragments of the peptide, which if required are suitably protected, and eliminating all protecting groups, if present, at the completion of the stepwise coupling to obtain the peptide of formula 1. More specific processes are illustrated in the examples hereinafter.

With reference to the preparation of peptides of formula 1 in which Z is 5-1H-tetrazolyl, the derived amino acid residue containing the tetrazole can be prepared as follows: Boc-Leu-NH$_2$, for example, was converted to its corresponding nitrile derivative by treatment with p-toluenesulfonyl chloride in methylenedichloride in the presence of excess pyridine and a catalytic amount of 4-dimethylaminopyridine (Fieser and Fieser, "Reagents for Organic Synthesis", John Wiley and Sons, Inc., New York, N.Y., USA, 1967, vol 1, p 1183). The nitric derivative then was mixed with tributyl tin azide, J. G. A. Luijten et at., Rec. Trav., 81, 202 (1962), giving a tetrazole tin intermediate [cf. K. Sisido et al., Journal of Organometallic Chemistry, 33, 337 (1971) and J. Dubois et al., J. Med. Chem., 27, 1230 (1984)]. The latter was treated with hydrogen chloride in diethyl ether to afford the desired tetrazole residue as a hydrochloride salt, for example, NH$_2$CH[CH$_2$CH(CH$_3$)$_2$]-5-1H-tetrazole dihydrochloride. The tetrazole residue, or its hydrochloride salt, was used for coupling with the appropriate amino acid or protected fragment, leading to the desired peptide of formula 1.

With reference to the preparation of peptides of formula 1 in which Y is 5-1H-tetrazolyl, the required tetrazole-containing derived amino acid residue, preferably, N-(tertiary-butyloxycarbonyl)-2(S)-amino-3-(5-1H-tetrazolyl)-propionic acid benzyl ester, was prepared in a similar fashion starting from commercially available N-(tertiary-butyloxycarbonyl)-2(S)-amino-3-cyanopropionic acid benzyl ester. Alternatively, a derived amino acid having a cyanomethyl side chain, e.g. N-(tertiary-butyloxycarbonyl)-2(S)-amino-3-cyanopropionic acid, can be coupled with other amino acid residues to give a protected pentapeptide intermediate. Subsequent transformation of the cyano group of the intermediate to a tetrazole is effected by treating the intermediate with tributyl tin azide. Thereafter, subsequent deprotection of the product affords the corresponding peptide of formula 1 in which Y is 5-1H-tetrazolyl.

N-alkylated amino acid residues required for the preparation of peptides of formula 1 in which $R^1$ and/or $R^4$ are lower alkyl or phenyl(lower)alkyl are commercially available, such as N-(tertiary-butyloxycarbonyl)-N-methylvaline, or can be prepared by known processes. For example, N-(tertiary-butyloxycarbonyl)-N-(alkyl or phenylalkyl)-valine residues can be prepared by the method of S. T. Cheung and L. Benoiton, Can. J. Chem., 55, 916 (1977) involving a reductive amination process using sodium cyanoborohydride, L-valine benzyl ester tosylate and the corresponding aldehyde. Tertiary-butyl-oxycarbonyl-N-methyl-amino acids also can be prepared by the method of R. K. Olsen, J. Org. Chem., 35, 1912 (1970) using methyl iodide and silver oxide.

The peptide of formula 1 of this invention can be obtained in the form of a therapeutically acceptable salt.

In the instance where a particular peptide has a residue which functions as a base, examples of such salts am those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phorphoric acid. If desired, a particular acid addition salt is convened into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In the instance where a particular peptide has one or more free carboxy groups, examples of such salts are those with the sodium, potassium or calcium cations, or with strong organic bases, for example, triethylamine or N-methylmorpholine.

Antiherpes Activity

The antiviral activity of the peptides of formula 1 can be demonstrated by biochemical, microbiological and biological procedures showing the inhibitory effect of the compounds on the replication of herpes simplex viruses, types 1 and 2 (HSV-1 and HSV-2), and other herpes viruses, for example, varicella zoster virus (VZV), Epstein-Burr virus (EBV), equine herpes virus (EHV) and cytomegalovirus.

Noteworthy is the fact that all of the aforementioned viruses are dependent on their own ribonucleotide reductase to synthesize deoxyribonucleotides for their replication. Although this fact may not be directly linked with the antiviral activity found for the present peptides, the latter compounds have been shown so far to have antiviral properties against all viruses dependent on ribonucleotide reductase to synthesis DNA for their replication.

In the examples hereinafter, the inhibitory effect on herpes ribonucleotide reductase is noted for exemplary peptides of formula 1. Noteworthy, in the connection with this specific inhibition of herpes ribonucleotide reductase, is the relatively minimal effect or absence of such an effect of the peptides on cellular ribonucleotide reductase activity required for normal cell replication.

A method for demonstrating the inhibitory effect of the peptides of formula I on viral replication is the cell culture technique; see, for example, T. Spector et at., Proc. Natl. Acad. Sci. USA, 82, 4254 (1985).

The therapeutic effect of the peptides can be demonstrated in laboratory animals, for example, by using an assay based on genital herpes infection in Swiss Webster mice, described by E. R. Kern, et at., Antiviral Research, 3, 253 (1983).

When a peptide of this invention, or one of its therapeutically acceptable salts, is employed as an antiviral agent, it is administered topically or systemically to warm-blooded animals, e.g. humans, pigs or hones, in a vehicle comprising one or more pharmaceutically acceptable carriers, the proportion of which is determined by the solubility and chemical nature of the peptide, chosen mute of administration and standard biological practice. For topical administration, the peptide can be formulated in pharmaceutically accepted vehicles containing 0.1 to 10 percent, preferably 0.5 to 5 percent, of the active agent. Such formulations can be in the form of a solution, cream or lotion.

For systemic administration, the peptide of formula 1 is administered by either intravenous, subcutaneous or intramuscular injection, in compositions with pharmaceutically acceptable vehicles or carriers. For administration by injection, it is preferred to use the peptide in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's Pharmaceutical Sciences", 16th ed, Mack Publishing Company, Easton, Pa., 1980.

The dosage of the peptide will vary with the form of administration and the particular active agent chosen. Furthermore, it will vary with the particular host under treatment. Generally, treatment is initiated with small increments until the optimum effect under the circumstances is reached. In general, the peptide is most desirably administered at a concentration level that will generally afford antivirally effective results without causing any harmful or deleterious side effects.

With reference to topical application, the peptide is administered cutaneously in a suitable topical formulation to the infected area of the body e.g. the skin or part of the oral or genital cavity, in an amount sufficient to cover the infected area. The treatment should be repeated, for example, every four to six hours until lesions heal. Healing results usually within 3 to 4 days. No contraindications have been observed.

With reference to systemic administration, the peptide of formula 1 is administered at a dosage of 10 mcg to 1000 mcg per kilogram of body weight per day, although the aforementioned variations will occur. However, a dosage level that is in the range of from about 100 mcg to 500 mcg per kilogram of body weight per day is most desirably employed in order to achieve effective results.

Another aspect of this invention comprises a cosmetic composition comprising a herpes vital prophylactic amount of the peptide of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nigh fly to susceptible areas of the skin. Generally, the cosmetic composition contains less of the peptide than corresponding pharmaceutical compositions for topical application. A preferred range of the amount of the peptide in the cosmetic composition is 0.01 to 0.2 percent by weight.

Although the formulation disclosed hereinabove are effective and relatively safe medications for treating herpes viral infections, the possible concurrent administration of these formulations with other antiviral medications or agents to obtain beneficial results is not excluded. Such other antiviral medications or agents include acyclovir and antiviral surface active agents or antiviral interferons such as those disclosed by S. S. Asculai and F. Rapp in U.S. Pat. No. 4,507,281, Mar. 26, 1985.

The following examples illustrate further this invention. Solution percentages or ratios express volume to volume relationship, unless stated otherwise. Abbreviations used in the examples include Boc: t-butyloxycarbonyl; BOP: (benzotriazol-1-yloxy)tris(dimethylamino)-phosphonium hexafluorophosphate; iBu: 2-methylpropyl; Bzl: benzyl; $CH_2Cl_2$: methylenedichloride; DAT: desaminotyrosyl or 1-oxo-3-(4-hydroxyphenyl)propyl; DIPEA: diisopropylethylamine; DCC: N,N-dicyclohexylcarbodiimide; DMF: dimethyl formamide; Et: ethyl; $Et_2O$: diethyl ether;, EtOH: ethanol; HOBt: 1-hydroxybenzouiazole; HPLC: high performance liquid chromatography: Me: methyl; MeOH: methanol; N-Me-Val: N-methylvalyl residue; $PhCH_2CH_2CO$: 1-oxo-3-phenylpropyl; $PhCH_2$-$CH_2CH_2CO$: 1-oxo-4-phenylbutyl; TFA: trifluoroacetic acid. Temperatures are given in degrees centigrade.

EXAMPLE 1

General Procedure for the Solid Phase Preparation of Formula 1

A modified version of the solid phase method of R. B. Merrifield, J. Am. Chem. Soc., 85, 2149 (1963) was used to prepare the peptides using preferably a BHA-photoresin Such as [4-(2-chloropropionyl)phenoxy]acetamidomethyl-copoly(styrene-1% divinyl-benzene) resin, see D. Bellof and M. Mutter, Chemia, 39, 317 (1985). Protection of free carboxy groups and hydroxy groups was provided by the Bzl protective group. Typically, a Boc-amino acid, representing the C-terminal unit of the desired peptide, e.g. Boc-Leu-OH, was linked to the above-noted photoresin by the potassium fluoride method of K. Horiki et at., Chem. Lett., 165 (1978), using 9 molar equivalents of KF and 3.6 molar equivalents of Boc-Leu-OH, for example in DMF at 70° C. for 24 hours, to give [4-{2-(Boc-leucine)-propionyl}phenoxy] acetamidomethyl-copoly(styrene-1% divinylbenzene) resin. The dried amino acid-solid support typically showed a leucine content of 0.6 to 0.8 mmol/g for the product, as determined by deprotection of an aliquot, followed by picric acid titration, B. F. Gisin, Anal. Chim. Acta, 58, 248 (1972). The latter amino acid-solid support was used to build up the required sequence of units (i.e. amino acid residues, derived amino acid residues) of the desired peptide by solid phase methodology. Two molar equivalents (per mole of the amino acid-solid support) of the appropriate amino acid residues were coupled serially to the solid support system using BOP (2 molar equivalents), or BOP (2 molar equivalents)/HOBt (1 molar equivalent), in the presence of N-methylmorpholine (6 molar equivalents) in dry DMF. Completion of coupling was verified by a negative ninhydrin test, E. Kaiser et al., Anal Biochem., 34, 595 (1979). Double coupling was used when necessary.

Cleavage of the protected peptide from the solid support was accomplished by irradiation at 330 nm in EtOH/DMF (1:4) at 0° under an argon atmosphere for 6 to 18 h. Protective groups (Bzl), if present, were removed from the cleavage product by hydrogenolysis over 5% or 10% Pd/C or 20% Pd(OH)$_2$/C by standard procedures (cf. example 1). Purification of the final product was performed by reversed-phase HPLC to better than 95% homogeneity using 0.06% aqueous TFA/acetonitrile gradients.

More specifically exemplified, the protected peptide, (SEQ ID NO:2) DAT-N-Me-Val-Ile-Asn-Asp(OBzl)-Leu-OH was assembled by the preceding procedure on a BHA photoresin using BOP/HOBt as the coupling agent, followed by cleavage of the resulting protected peptide resin by photolysis under argon at −5° for 6 h. DMF:EtOH (4:1) was used as the photolysis medium. Deprotection of the cleavage product was effected by hydrogenolysis using 5% Pd/C as catalyst. Purification of the product was done by HPLC, the product being dissolved in 0.1N aqueous NH$_4$OH and the solution adjusted to pH6 with 0.1N aqueous AcOH. Whatman Partisil ® 100DS-3 C-18 column (2.2×50 cm$^2$), 10 micron particle size, was used. Elution was done with gradients of acetonitrile and 0.06% aqueous TFA. Pure fractions (determined by analytical HPLC) were pooled and lyophilized to give (SEQ ID NO:3) DAT-N-Me-Val-Ile-Asn-Asp-Leu-OH. MS: 735 (M+H)$^+$.

The above procedure was used to prepare the peptides listed in the table of example 5. Commercially available Boc-amino acids were used. Unnatural amino acids were used in their Boc protected form; they were either commercially available, readily prepared from commercially available corresponding amino acids by reaction with di-tertiary-butyl carbonate, or prepared by standard methods. Modifications of the procedure for the preparation of terminal tetrazole peptides of formula 1 wherein Z is 5-1H-tetrazolyl and tetrazole peptides of formula 1 wherein Y is 5-1H-tetrazolyl are illustrated in the following two examples.

EXAMPLE 2

Preparation of (SEQ ID NO:1) PhCH$_2$CH$_2$CO-N-Me-Val-Ile-Asn-Asp-NHCH[CH$_2$CH(CH$_3$)$_2$]-5-1H-tetrazole A modified procedure of example I was used to assemble the protected tetrapeptide (SEQ ID NO:5) PhCH$_2$CH$_2$CO-N-Me-Val-Ile-Asn-Asp(OBzl)-OH wherein Boc-Asp(OBzl)-OH was linked to the photo-resin and HOBt/DCC was used for coupling Boc-Asn-OH. A solution of the protected tetrapeptide (375 mg, 0.54 mmol) and 3-methyl-1(S)-(5-1H-tetrazolyl)butylamine (375 mg, 1.25 mmol) in DMF (15 ml) was cooled to 0. DIPEA (284 mg) and then diphenylphosphoryl azide (760 mg) were added to the solution. The reaction mixture was stirred for 16 h at 0 and then partitioned between Et$_2$O and H$_2$O containing of few drops of concentrated NH$_4$OH (pH=9.5). The aqueous phase was separated, washed with fresh Et$_2$O and filtered through a 45 m membrane. The pH of the filtrate was adjusted to pH 6.5 by the addition of AcOH and again filtered through a 45 m membrane. The filtrate was loaded on a HPLC preparatory column. The column was eluted with a continuous gradient of 0.06% aqueous TFA in acetonitrile. The pure fractions as indicated by analytical HPLC were combined and lyophilized to give the corresponding Asp(OBzl) protected peptide (132 mg) of the title compound.

The latter compound (112 mg) was subjected to hydrogenolysis at one atmosphere of pressure at room temperature [5% Pd/C (100 mg) in EtOH (30 ml) for 16 h]. The reaction mixture was filtered and the filtrate concentrated to dryness under reduced pressure. The residue was dissolved in acetonitrile and H$_2$O. The acetonitrile was removed from the solution by distillation under reduced pressure. Lyophization of the resultant concentrate gave the title compound (88 mg) as a white powder which was 90% pure as indicated by analytical HPLC. FAB/MS: 743(M+1)$^+$.

EXAMPLE 3

Preparation of (SEQ ID NO:6) PhCH$_2$CH$_2$CO-N-Me-Val-Ile-NHCH[CH$_2$-5-1H-tetrazole]CO-Asp-Leu-OH The intermediate (SEQ ID NO:7) PhCH$_2$CH$_2$CO-N-Me-Val-Ile-NHCH-(CH$_2$CN)CO-Asp-Leu-OH was prepared by following the procedure of example 1 and the appropriate Boc amino acids (including the commercially available Boc-NHCH(CH$_2$CN)COOH). All couplings were done with BOP/HOBt. The intermediate (40 mg) and tributyltin azide (100 mg) in anhydrous tetrahydrofuran were heated in a sealed tube at 80 to 90 for 4 days. The tube was cooled and opened. Solvent was removed from the contents by evaporation under reduced pressure.

The residue was suspended in anhydrous Et$_2$O and gaseous HCl was bubbled into the mixture for 45 min. After evaporation of the Et$_2$O, the solid residue was triturated with hexane, and then dissolved in EtOH. The solution was filtered and the filtrate evaporated to give 35 mg of a white solid. The solid was dissolved in H$_2$O-acetonitrile (1:1, 3.7 ml) and the solution injected into a semi-prep HPLC. Elution with gradients of 0.06% aqueous TFA and acetonitrile afforded the Asp(OBzl) protected peptide of the title compound. Deprotection of the protected peptide by hydrogenolysis according to the condition described in example 2 afforded the title compound (10.6 mg) which was 100% pure as indicated by analytical HPLC. FAB/MS: 744 (M+1)$^+$.

EXAMPLE 4

Preparation of the Intermediate Boc-Asp(OBzl)ψ[CSNH]Leu-OBzl (An example of the procedure used to prepare thioamide intermediates for the preparation of peptides of formula 1 wherein W is thioxo.)

A stirred mixture of Boc-Asp(OBzl)Leu-OBzl (2.90 g, 5.51 mmol) and Lawesson's reagent (1.12 g, 2.7 mmol), see U. Pederson et al., Tetrahedron, 38, 3267 (1982), in toluene (30ml) was heated at reflux for 2h. Column chromatography with SiO$_2$ (3.5×30 cm) and elution with CH$_2$Cl$_2$ gave the title compound (2.0 g), MS: 543 (M+H)$^+$, as yellow oil (major fraction).

Analogous thioamides were prepared in the same manner and incorporated into the appropriate peptides of formula 1 according to conventional solution phase peptide synthesis.

EXAMPLE 5

Inhibition of Herpes Simplex Virus (HSV, type 1) Ribonucleotide Reductase a. Preparation of Enzyme HSV-1 ribonucleotide reductase (partially purified) was obtained from quiescent BHK-21/C13 cells infected with strain F HSV-1 virus at 10 plaque forming units/ cell as described by E. A. Cohen et al., J. Gen. Virol., 66, 733 (1985).

b) Assay and Results for Exemplified Peptides

By following the procedure described by P. Gaudreau et al., J. Biol. Chem., 262, 12413 (1987), the assay results listed in the following table were obtained. The assay result for each peptide is expressed as the concentration of the peptide producing 50% of the maximal inhibition ($IC_{50}$) of enzyme activity. The number of units of the enzyme preparation used in each assay was constant, based on the specific activity of the enzyme preparation. The results are relative to the activity obtained in control experiments without peptide and represent the mean of four assays that varied less than 10% with each other.

TABLE (SEQ ID NO:8)
$XNR^1CH(R^2)$—CO—Ile—NH—$CH(CH_2Y)$—CO—Asp—$NHCH(R^7)$—Z
(Peptides of formula 1 wherein X, $R^1$, Y and Z are as shown below, $R^2$ is $CH(CH_3)_2$, $R^3$ is $CH(CH_3)C_2H_5$, $R^4$, $R^5$ and $R^6$ are hydrogen, $R^7$ is $CH_2CH_2CH(CH_3)_2$ and W is O)

| X | $R^1$ | Y | Z | FAB/MS (M+H)* | $IC_{50}$ (µM) |
|---|---|---|---|---|---|
| $CH_3CO$ | $PhCH_2CH_2$ | $CONH_2$ | COOH | 719 | 17 |
| $(CH_3)_2CHCH_2CH_2CO$ | $CH_3$ | $CONH_2$ | COOH | 685 | 7.6 |
| 2-(biphenylyl)carbonyl | $CH_3$ | $CONH_2$ | COOH | 767 | 2.5 |
| 2-(phenylmethyl)benzoyl | $CH_3$ | $CONH_2$ | COOH | 781 | 5.5 |
| $PhCH_2CH_2CH_2CO$ | $CH_3$ | $CONH_2$ | COOH | 733 | 6.2 |
| $PhCH_2CH_2CO$ | $CH_3$ | $CONH_2$ | 5-1H-t* | 743 | 3.8 |
| $PhCH_2CH_2CO$ | $CH_3$ | 5-1H-t* | COOH | 744 | 2.0 |
| DAT | $CH_3$ | $CONH_2$ | COOH | 735 | 6.0 |

*5-1H-t represents 5-1H-tertrazolyl

Other examples of the peptides of formula 1 are:

| | |
|---|---|
| $PhCH_2CH_2CO$—N—Me—Val—Ile—Asp—Asp—Leu—OH | (SEQ ID NO:9) |
| $PhCH_2CH_2CO$—N—Et—Val—Ile—Asn—Asp—Leu—OH | (SEQ ID NO:10) |
| $PhCH_2CH_2CO$—N-iBu-Val—Ile—Asn—Asp—Leu—OH | (SEQ ID NO:11) |
| $PhCH_2CH_2CO$—N—Me—Val—Ile—Asn—Asp—Leu—OH | (SEQ ID NO:12) |
| (3,4-dihydroxy-Ph)$CH_2CH_2CO$—N—Me—Val—Ile—Asn—Asp—Leu—OH | (SEQ ID NO:13) |
| [2-(2'-carboxy)biphenylyl]carbonyl-N—Me—Val—Ile—Asn—Asp—Leu—OH | (SEQ ID NO:14) |
| $PhCH_2CH_2CO$—N—Me—Thr—Ile—Asn—AspΨ[CSNH]Leu—OH | (SEQ ID NO:15) |

---

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /label=Peptide
      / note= "The amino acid at position 1 is XNR1-CH(R2)-C(O), wherein X is (1-10C)alkanoyl, (1-10C)alkoxycarbonyl, benzoyl, benzoyl monosubstituted or disubstituted with a substituent selected from halo, hydroxy, lower alkyl, lower alkoxy, phenyl, 2-carboxyphenyl or benzyl, 2,2- diphenylacetyl, phenyl(2-10C)alkanoyl or phenyl(2- 10C)alkanoyl monosubstituted or disubstituted on the aromatic portion thereof with a substituent selected from halo, hydroxy, lower alkyl, lower alkoxy or phenyl; wherein the R1 is lower alkyl or phenyl(lower)alkyl and wherein R2 is lower alkyl or hydroxy(lower)alkyl."

( i x ) FEATURE:
    ( A ) NAME/KEY: Peptide ( B ) LOCATION: 2
                ( D ) OTHER INFORMATION: /label=Peptide
                        / note= "The amino acid at position 2 is NH-CH(R3)-C(O),
                        wherein R3 is hydrogen, lower alkyl, hydroxy(lower)
                        alkyl, mercapto(lower)alkyl, methoxy(lower)alkyl,
                        methylthio(lower)alkyl, lower cycloalkyl or (lower
                        cycloalkyl) methyl."

( i x ) FEATURE:
                ( A ) NAME/KEY: Peptide
                ( B ) LOCATION: 3
                ( D ) OTHER INFORMATION: /label=Peptide
                        / note= "The amino acid at position 3 is NR4-CH(CH2Y)-CO,
                        wherein R4 is hydrogen or lower alkyl, and wherein Y is
                        carboxy, carbamyl, or 5-1H-tetrazolyl."

( i x ) FEATURE:
                ( A ) NAME/KEY: Peptide
                ( B ) LOCATION: 4
                ( D ) OTHER INFORMATION: /label=Peptide
                        / note= "The amino acid at position 4 is
                        NH-CH-[CR5(R6)-COOH]-C(W), wherein R5 and R6 are each
                        independently hydrogen or lower alkyl, and wherein W is
                        oxo or thioxo."

( i x ) FEATURE:
                ( A ) NAME/KEY: Peptide
                ( B ) LOCATION: 5
                ( D ) OTHER INFORMATION: /label=Peptide
                        / note= "The amino acid at position 5 is NH-CH(R7)-Z,
                        wherein R7 is lower alkyl, and wherein Z is carboxy
                        or 5-1H- tetrazolyl."

( x i ) SEQUENCE DESCRIPTION: SEQ ID NO:1:

Xaa  Xaa  Xaa  Xaa  Xaa
        1                       5

( 2 ) INFORMATION FOR SEQ ID NO:2:

( i ) SEQUENCE CHARACTERISTICS:
                ( A ) LENGTH: 5 amino acids
                ( B ) TYPE: amino acid
                ( D ) TOPOLOGY: linear ( i x ) FEATURE:
                ( A ) NAME/KEY: Peptide
                ( B ) LOCATION: 1
                ( D ) OTHER INFORMATION: /label=Peptide
                        / note= "The amino acid at position 1 is DAT-N-Me-Val,
                        wherein DAT is desaminotyrosyl or 1-oxo-3-(4-
                        hydroxyphenyl)propyl, and wherein N-Me-Val is
                        N- methylvalyl."

( i x ) FEATURE:
                ( A ) NAME/KEY: Peptide
                ( B ) LOCATION: 4
                ( D ) OTHER INFORMATION: /label=Peptide
                        / note= The amino acid at position 4 is Asp(OBzl),
                        wherein (OBzl) is a Benzylether."

( x i ) SEQUENCE DESCRIPTION: SEQ ID NO:2:

Xaa  Ile  Asn  Xaa  Leu
        1                       5

( 2 ) INFORMATION FOR SEQ ID NO:3:

( i ) SEQUENCE CHARACTERISTICS:
                ( A ) LENGTH: 5 amino acids
                ( B ) TYPE: amino acid
                ( D ) TOPOLOGY: linear ( i x ) FEATURE:
                ( A ) NAME/KEY: Peptide
                ( B ) LOCATION: 1
                ( D ) OTHER INFORMATION: /label=Peptide
                        / note= "The amino acid at position 1 is DAT-N-Me-Val, wherein DAT is desaminotyrosyl or 1-oxo-3-(4-hydroxyphenyl)propyl, and wherein N-Me-Val is N-methylvalyl."

( x i ) SEQUENCE DESCRIPTION: SEQ ID NO:3:

Xaa  Ile  Asn  Asp  Leu
1                      5

( 2 ) INFORMATION FOR SEQ ID NO:4:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /label=Peptide
         / note="The amino acid at position 1 is
         PhCH2CH2CO-N- Me-Val, wherein N-Me-Val is N-methylvalyl."

( i x ) FEATURE:
    ( A ) NAME/KEY: Peptide
    ( B ) LOCATION: 4
    ( D ) OTHER INFORMATION: /label=Peptide
         / note= "The amino acid at position 4 is
         Asp-NHCH[CH2-CH(CH3)2]-5-1H-tetrazole."

( x i ) SEQUENCE DESCRIPTION: SEQ ID NO:4:

Xaa  Ile  Asn  Xaa
1

( 2 ) INFORMATION FOR SEQ ID NO:5:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /label=Peptide
         / note="The amino acid at position 1 is
         PhCH2CH2CO-N- Me-Val, wherein N-Me-Val is N-methylvalyl."

( i x ) FEATURE:
    ( A ) NAME/KEY: Peptide
    ( B ) LOCATION: 4
    ( D ) OTHER INFORMATION: /label=Peptide
         / note= "The amino acid at position 4 is Asp(OBzl)-OH,
         wherein (OBzl) is a Benzylether."

( x i ) SEQUENCE DESCRIPTION: SEQ ID NO:5:

Xaa  Ile  Asn  Xaa
1

( 2 ) INFORMATION FOR SEQ ID NO:6:

( i ) SEQUENCE CHARACTERISTICS:
    ( A ) LENGTH: 5 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /label=Peptide
         / note= "The amino acid at position 1 is
         PhCH2CH2CO-N- Me-Val, wherein N-Me-Val is N-methylvalyl."

( i x ) FEATURE:
    ( A ) NAME/KEY: Peptide (B) LOCATION: 3
(D) OTHER INFORMATION: /label=Peptide
/ note= "The amino acid at position 3 is NHCH[CH2-5-1H-
tetrazole]CO."

(xi) SEQUENCE DESCRIPTION: SEQ ID NO:6:

Xaa Ile Xaa Asp Leu
1               5

(2) INFORMATION FOR SEQ ID NO:7:

(i) SEQUENCE CHARACTERISTICS:
  (A) LENGTH: 5 amino acids
  (B) TYPE: amino acid
  (D) TOPOLOGY: linear (ix) FEATURE:
  (A) NAME/KEY: Peptide
  (B) LOCATION: 1
  (D) OTHER INFORMATION: /label=Peptide
    / note= "The amino acid at position 1 is
    PhCH2CH2CO-N- Me-Val, wherein N-Me-Val is N-methylvalyl."

(ix) FEATURE:
  (A) NAME/KEY: Peptide
  (B) LOCATION: 3
  (D) OTHER INFORMATION: /label=Peptide
    / note= "The amino acid at position 3 is NHCH-(CH2CN)CO."

(xi) SEQUENCE DESCRIPTION: SEQ ID NO:7:

Xaa Ile Xaa Asp Leu
1               5

(2) INFORMATION FOR SEQ ID NO:8:

(i) SEQUENCE CHARACTERISTICS:
  (A) LENGTH: 5 amino acids
  (B) TYPE: amino acid
  (D) TOPOLOGY: linear (ix) FEATURE:
  (A) NAME/KEY: Peptide
  (B) LOCATION: 1
  (D) OTHER INFORMATION: /label=Peptide
    / note= "The amino acid at position 1 is XNR1-CH(R2)-CO,
    wherein X is CH3CO, (CH3)2CHCH2CH2CO,
    2- (biphenylyl)carbonyl, 2-(phenylmethyl)benzoyl,
    PhCH2CH2CH2CO, PhCH2CH2CO, desaminotyrosyl or
    1-oxo-3-(4- hydroxyphenyl)propyl;
    wherein R1 is PhCH2CH2 or CH3, and wherein R2 is
    CH(CH3)2."

(ix) FEATURE:
  (A) NAME/KEY: Peptide
  (B) LOCATION: 3
  (D) OTHER INFORMATION: /label=Peptide
    / note= "The amino acid at position 3 is NH-CH(CH2Y)-CO
    wherein Y is CONH2 or 5-1H-tetrazolyl."

(ix) FEATURE:
  (A) NAME/KEY: Peptide
  (B) LOCATION: 5
  (D) OTHER INFORMATION: /label=Peptide
    / note= "The amino acid at position 5 is NHCH(R7)-Z,
    wherein R7 is CH2CH2CH(CH3)2, and wherein Z is COOH or
    5-1H- tetrazolyl."

(xi) SEQUENCE DESCRIPTION: SEQ ID NO:8:

Xaa Ile Xaa Asp Xaa
1               5

(2) INFORMATION FOR SEQ ID NO:9:

(i) SEQUENCE CHARACTERISTICS:

(A) LENGTH: 5 amino acids
(B) TYPE: amino acid
(D) TOPOLOGY: linear (ix) FEATURE:
    (A) NAME/KEY: Peptide
    (B) LOCATION: 1
    (D) OTHER INFORMATION: /label=Peptide
        / note= "The amino acid at position 1 is
        PhCH2CH2CO-N- Me-Val, wherein N-Me-Val is N-methylvalyl."

(xi) SEQUENCE DESCRIPTION: SEQ ID NO:9:

Xaa Ile Asp Asp Leu
1                 5

(2) INFORMATION FOR SEQ ID NO:10:

(i) SEQUENCE CHARACTERISTICS:
    (A) LENGTH: 5 amino acids
    (B) TYPE: amino acid
    (D) TOPOLOGY: linear (ix) FEATURE:
    (A) NAME/KEY: Peptide
    (B) LOCATION: 1
    (D) OTHER INFORMATION: /label=Peptide
        / note= "The amino acid at position 1 is
        PhCH2CH2CO-N- Et-Val, wherein N-Et is N-Ethyl."

(xi) SEQUENCE DESCRIPTION: SEQ ID NO:10:

Xaa Ile Asn Asp Leu
1                 5

(2) INFORMATION FOR SEQ ID NO:11:

(i) SEQUENCE CHARACTERISTICS:
    (A) LENGTH: 5 amino acids
    (B) TYPE: amino acid
    (D) TOPOLOGY: linear (ix) FEATURE:
    (A) NAME/KEY: Peptide
    (B) LOCATION: 1
    (D) OTHER INFORMATION: /label=Peptide
        / note= "The amino acid at position 1 is
        PhCH2CH2CO-N- iBu-Val, wherein iBu is 2-methylpropyl."

(xi) SEQUENCE DESCRIPTION: SEQ ID NO:11:

Xaa Ile Asn Asp Leu
1                 5

(2) INFORMATION FOR SEQ ID NO:12:

(i) SEQUENCE CHARACTERISTICS:
    (A) LENGTH: 5 amino acids
    (B) TYPE: amino acid
    (D) TOPOLOGY: linear (ix) FEATURE:
    (A) NAME/KEY: Peptide
    (B) LOCATION: 1
    (D) OTHER INFORMATION: /label=Peptide
        / note= "The amino acid at position 1 is
        PhCH2CH2CO-N- Me-Val, wherein N-Me-Val is N-methylvalyl."

(xi) SEQUENCE DESCRIPTION: SEQ ID NO:12:

Xaa Ile Asn Asp Leu
1                 5

(2) INFORMATION FOR SEQ ID NO:13:

(i) SEQUENCE CHARACTERISTICS:

(A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /label=Peptide
                        /note= "The amino acid at position 1 is
                        (3,4-dihydroxy-Ph)CH2 CH2CO-N-Me-Val, wherein N-Me-Val
                        is N-methylvalyl."

(xi) SEQUENCE DESCRIPTION: SEQ ID NO:13:

Xaa Ile Asn Asp Leu
        1                 5

(2) INFORMATION FOR SEQ ID NO:14:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /label=Peptide
                        /note= "The amino acid at position 1 is [2-(2'-
                        carboxy)biphenylyl]carbonyl-N-Me-Val, wherein N-Me-Val
                        is N-methylvalyl."

(xi) SEQUENCE DESCRIPTION: SEQ ID NO:14:

Xaa Ile Asn Asp Leu
        1                 5

(2) INFORMATION FOR SEQ ID NO:15:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /label=Peptide
                        /note= "The animo acid at position 1 is
                        PhCH2CH2CO-N-Me-Thr, wherein N-Me-Thr is
                        N-Methylthreonine."

(ix) FEATURE:
                (A) NAME/KEY: Peptide
                (B) LOCATION: 4
                (D) OTHER INFORMATION: /label=Peptide
                        /note= "The amino acid at position 4 is Asp [CSNH]."

(xi) SEQUENCE DESCRIPTION: SEQ ID NO:15:

Xaa Ile Asn Xaa Leu
        1                 5

(2) INFORMATION FOR SEQ ID NO:16:

(i) SEQUENCE CHARACTERISTICS:
                (A) LENGTH: 5 amino acids
                (B) TYPE: amino acid
                (D) TOPOLOGY: linear (ix) FEATURE:
                (A) NAME/KEY: Peptide
                (B) LOCATION: 1
                (D) OTHER INFORMATION: /label=Peptide
                        /note= "The amino acid at position 1 is DAT-N-Me-Val,
                        wherein DAT is desaminotyrosyl or 1-oxo-3-(4-
                        hydroxyphenyl)propyl, and wherein N-Me-Val is N- methylvalyl."

( x i ) SEQUENCE DESCRIPTION: SEQ ID NO:16:

Xaa Ile Asn Asp Leu
1               5

( 2 ) INFORMATION FOR SEQ ID NO:17:

( i ) SEQUENCE CHARACTERISTICS:
      ( A ) LENGTH: 5 amino acids
      ( B ) TYPE: amino acid
      ( D ) TOPOLOGY: linear ( i x ) FEATURE:
      ( A ) NAME/KEY: Peptide
      ( B ) LOCATION: 1
      ( D ) OTHER INFORMATION: /label=Peptide
          / note= "The amino acid at position 1 is CH3CO-(N-phenylethyl- Val)."

( x i ) SEQUENCE DESCRIPTION: SEQ ID NO:17:

Xaa Ile Asn Asp Leu
1               5

( 2 ) INFORMATION FOR SEQ ID NO:18:

( i ) SEQUENCE CHARACTERISTICS:
      ( A ) LENGTH: 5 amino acids
      ( B ) TYPE: amino acid
      ( D ) TOPOLOGY: linear ( i x ) FEATURE:
      ( A ) NAME/KEY: Peptide
      ( B ) LOCATION: 1
      ( D ) OTHER INFORMATION: /label=Peptide
          / note= "The amino acid at position 1 is ( C H 3 )2CHCH2CH2CO-N-Me-Val, wherein N-Me-Val is N- methylvalyl."

( x i ) SEQUENCE DESCRIPTION: SEQ ID NO:18:

Xaa Ile Asn Asp Leu
1               5

( 2 ) INFORMATION FOR SEQ ID NO:19:

( i ) SEQUENCE CHARACTERISTICS:
      ( A ) LENGTH: 5 amino acids
      ( B ) TYPE: amino acid
      ( D ) TOPOLOGY: linear ( i x ) FEATURE:
      ( A ) NAME/KEY: Peptide
      ( B ) LOCATION: 1
      ( D ) OTHER INFORMATION: /label=Peptide
          / note= "The amino acid at position 1 is 2- (biphenylyl)carbonyl-N-Me-Val, wherein N-Me-Val is N- methylvalyl."

( x i ) SEQUENCE DESCRIPTION: SEQ ID NO:19:

Xaa Ile Asn Asp Leu
1               5

( 2 ) INFORMATION FOR SEQ ID NO:20:

( i ) SEQUENCE CHARACTERISTICS:
      ( A ) LENGTH: 5 amino acids
      ( B ) TYPE: amino acid
      ( D ) TOPOLOGY: linear ( i x ) FEATURE:
      ( A ) NAME/KEY: Peptide
      ( B ) LOCATION: 1

(D) OTHER INFORMATION: /label=Peptide
/ note= "The amino acid at position 1 is
2- (phenylmethyl)benzoyl-N-Me-Val, wherein N-Me-Val
is N- methylvalyl."

(xi) SEQUENCE DESCRIPTION: SEQ ID NO:20:

Xaa Ile Asn Asp Leu
1                 5

(2) INFORMATION FOR SEQ ID NO:21:

(i) SEQUENCE CHARACTERISTICS:
    (A) LENGTH: 5 amino acids
    (B) TYPE: amino acid
    (D) TOPOLOGY: linear (ix) FEATURE:
    (A) NAME/KEY: Peptide
    (B) LOCATION: 1
    (D) OTHER INFORMATION: /label=Peptide
        / note= "The amino acid at position 1 is
        PhCH2CH2CH2CO-N-Me-Val, wherein N-Me-Val is
        N- methylvalyl."

(xi) SEQUENCE DESCRIPTION: SEQ ID NO:21:

Xaa Ile Asn Asp Leu
1                 5

(2) INFORMATION FOR SEQ ID NO:22:

(i) SEQUENCE CHARACTERISTICS:
    (A) LENGTH: 4 amino acids
    (B) TYPE: amino acid
    (D) TOPOLOGY: linear (ix) FEATURE:
    (A) NAME/KEY: Peptide
    (B) LOCATION: 1
    (D) OTHER INFORMATION: /label=Peptide
        / note= "The amino acid at position 1 is
        PhCH2CH2CO-N- Me-Val, wherein N-Me-Val is N-methylvalyl."

(ix) FEATURE:
    (A) NAME/KEY: Peptide
    (B) LOCATION: 4
    (D) OTHER INFORMATION: /label=Peptide
        / note= "The amino acid at position 4 is
        Asp-NHCH[CH2CH(CH3)2]-5-1H-tetrazole."

(xi) SEQUENCE DESCRIPTION: SEQ ID NO:22:

Xaa Ile Asn Xaa
1

(2) INFORMATION FOR SEQ ID NO:23:

(i) SEQUENCE CHARACTERISTICS:
    (A) LENGTH: 5 amino acids
    (B) TYPE: amino acid
    (D) TOPOLOGY: linear (ix) FEATURE:
    (A) NAME/KEY: Peptide
    (B) LOCATION: 1
    (D) OTHER INFORMATION: /label=Peptide
        / note= "The amino acid at position 1 is
        PhCH2CH2CO-N- Me-Val, wherein N-Me-Val is N-methylvalyl."

(ix) FEATURE:
    (A) NAME/KEY: Peptide
    (B) LOCATION: 3
    (D) OTHER INFORMATION: /label=Peptide
        / note= "The amino acid at position 3 is NHCH[CH2-(5-1H-
        tetrazolyl)]-CO."

( x i ) SEQUENCE DESCRIPTION: SEQ ID NO:23:

Xaa Ile Xaa Asp Leu
1                 5

( 2 ) INFORMATION FOR SEQ ID NO:24:

( i ) SEQUENCE CHARACTERISTICS:
  ( A ) LENGTH: 5 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /label=Peptide
    / note= "The amino acid at position 1 is XNR1-CH(R2)-C(O),
    wherein X is a terminal group, for example, alkanoyl or
    phenylalkanoyl radicals, wherein R1 is alkyl or
    phenylalkyl, and wherein R2 is selected from the side
    chains of amino acid or derived amino acid residues."

( i x ) FEATURE:
  ( A ) NAME/KEY: Peptide
  ( B ) LOCATION: 2
  ( D ) OTHER INFORMATION: /label=Peptide
    / note= "The amino acid at position 2 is NH-CH(R3)-C(O),
    wherein R3 is selected from the side chains of amino acid
    or derived amino acid residues."

( i x ) FEATURE:
  ( A ) NAME/KEY: Peptide
  ( B ) LOCATION: 3
  ( D ) OTHER INFORMATION: /label=Peptide
    / note= "The amino acid at position 3 is NR4-CH(CH2Y)-CO,
    wherein R4 is hydrogen or lower alkyl, and wherein Y is
    carboxy, carbamyl or 5-1H-tetrazolyl."

( i x ) FEATURE:
  ( A ) NAME/KEY: Peptide
  ( B ) LOCATION: 4
  ( D ) OTHER INFORMATION: /label=Peptide
    / note= "The amino acid at position 4 is NH-CH[CR5(R6)-
    COOH]- C(W), wherein R5 is hydrogen or lower alkyl,
    wherein R6 is hydrogen or lower alkyl, and wherein
    W is oxo or thioxo."

( i x ) FEATURE:
  ( A ) NAME/KEY: Peptide
  ( B ) LOCATION: 5
  ( D ) OTHER INFORMATION: /label=Peptide
    / note= "The amino acid at position 5 is NH-CH(R7)-Z,
    wherein R7 is selected from the side chains of amino
    acid or derived amino acid residues, and wherein Z is
    carboxy or 5- 1H-tetrazolyl."

( x i ) SEQUENCE DESCRIPTION: SEQ ID NO:24:

Xaa Xaa Xaa Xaa Xaa
1               5

---

The embodiments of this invention in which an exclusive property or privilege is claimed are defined as follows:

1. A peptide selected from the group consisting of:

DAT—N—Me—Val—Ile—Asn—Asp—Leu—OH

CH$_3$CO—(N-phenylethyl—Val)—Ile—Asn—Asp—Leu—OH (CH$_3$)$_2$CHCH$_2$CH$_2$CO—N—Me—Val—Ile—Asn—Asp—Leu—OH 2-(biphenyl)carbonyl—N—Me—Val—Ile—Asn—Asp—Leu—OH 2-(phenylmethyl)benzoyl—N—Me—Val—Ile—Asn—Asp—Leu—OH PhCH$_2$CH$_2$CH$_2$CO—N—Me—Val—Ile—Asn—Asp—Leu—OH PhCH$_2$CH$_2$CO—N—Me—Val—Ile—Asn—Asp—NHCH[CH$_2$CH(CH$_3$)$_2$]-5-1H-tetrazole and PhCH$_2$CH$_2$CO—N—Me—Val—Ile—NHCH[CH$_2$—(5-1H-tetrazolyl)]—CO—Asp—Leu—OH or a therapeutically acceptable salt thereof.

2. A pharmaceutical composition comprising a peptide as recited in claim 1, or a therapeutically acceptable salt thereof, and pharmaceutically or veterinarily acceptable carrier.

3. A cosmetic composition comprising a peptide as recited in claim 1, or a therapeutically acceptable salt thereof, and pharmaceutically or veterinarily acceptable carrier.

4. A method of treating a herpes viral infection in a mammal comprising administering thereto an effective amount of a peptide as recited in claim 1, or a therapeutically acceptable salt thereof.

5. A method of claim 4 wherein the herpes viral infection is a herpes simplex viral infection.

6. A method of inhibiting the replication of herpes virus comprising contacting the virus with a herpes viral ribonucleotide reductase inhibiting amount of the peptide as recited in claim 1, or a therapeutically acceptable salt thereof.

* * * * *